(12) United States Patent
Ja

(10) Patent No.: US 7,397,043 B2
(45) Date of Patent: Jul. 8, 2008

(54) STANDOFF OPTICAL DETECTION PLATFORM BASED ON SURFACE PLASMON-COUPLED EMISSION

(75) Inventor: Shiou-Jyh Ja, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 163 days.

(21) Appl. No.: 11/335,140

(22) Filed: Jan. 19, 2006

(65) Prior Publication Data

US 2006/0255292 A1 Nov. 16, 2006

Related U.S. Application Data

(60) Provisional application No. 60/647,157, filed on Jan. 26, 2005.

(51) Int. Cl.
*H05B 33/00* (2006.01)
(52) U.S. Cl. .................................. 250/484.2
(58) Field of Classification Search ............... 250/484.2
See application file for complete search history.

(56) References Cited

U.S. PATENT DOCUMENTS

2005/0053974 A1* 3/2005 Lakowicz et al. ............... 435/6

OTHER PUBLICATIONS

Lakowicz, Radiative decay engineering 3. Surface plasmon-coupled directional emission,2003,Analytical Biochemistry,324,153-169.*
Gryczynski et al., Radiative decay engineering 4. Experimental studies of surface plasmon-coupled directional emission,2003,Analytical Biochemistry,324,170-182.*
J. R. Lakowicz, "Radiative decay engineering 3. Surface plasmon-coupled directional emission," *Analytical Biochemistry*, 324, pp. 153-169, (2004).

I. Gryczynski, J. Malicka, Z. Gryczynski, and J. R. Lakowicz, "Radiative decay engineering 4. Experimental studies of surface plasmon-coupled directional emission," *Analytical Biochemistry*, 324, pp. 170-182, (2004).

Jorg Enderlein, Thomas Ruckstuhl, and Stefan Seeger, "Highly efficient optical detection of surface-generated fluorescence," *Applied Optics*, vol. 38, issue 4, pp. 724-732, (1999).

(Continued)

*Primary Examiner*—David P. Porta
*Assistant Examiner*—Djura Malevic
(74) *Attorney, Agent, or Firm*—Dunlap, Codding & Rogers, P.C.

(57) ABSTRACT

A free-space standoff optical detection platform for any detection scheme based on spontaneous emissions, such as for example, fluorescence detection. More particularly, the present invention relates to a detection system having SPCE beads. In one embodiment, the SPCE beads are dielectric spheres coated with a thin metal layer, which supports surface plasmon resonance (SPR) at the operation wavelength. For fluorescence detection, fluorescence reporters can be coated outside of SPCE beads. Upon the presence of the analyte, the fluorescence reporter changes its emitting signal. The SPCE beads amplify the field strength of the excitation via the lens effect and SPR enhancement. The spontaneous emitting signal is collected via the coupling between the SPR and emission, which results high collection efficiency and signal-to-noise ratio. This surface plasmon-coupled emission (SPCE) signal propagates in the beads in a curved path dictated by the SPR condition. Finally, the SPCE signal is collimated by the beads and sent back to the standoff interrogator. Further, the SPCE beads may be spread over the target region and interrogated over a distance.

10 Claims, 6 Drawing Sheets

OTHER PUBLICATIONS

J. Enderlein, "Single-molecule fluorescence near a metal layer," *Chemical Physics*, 247, pp. 1-9, (1999).

W. H. Weber and C. F. Eagen, "Energy transfer from an excited dye molecule to the surface plasmons of an adjacent metal," *Optical Letters*, vol. 4, issue 8, pp. 236-238, (1979).

G. W. Ford and W. H. Weber, "Electromagnetic interactions of molecules with metal surfaces," *Physics Reports*, vol. 113, No. 4, pp. 195-287, Nov. 1984.

R. W. Gruhike and D. G. Hall, "Transmission of molecular fluorescence through a thin metal film by surface plasmons," *Applied Physics Letters*, vol. 53, No. 12, pp. 1041-1042, Sep. 1988.

R. E. Benner, R. Dornhaus, and R. K. Chang, "Angular emission profiles of dye molecules excited by surface plasmon waves at a metal surface," *Optics Communications*, vol. 30, Issue 2, pp. 145-149, Aug. 1979.

S. C. Kitson, W. L. Barnes, and J. R. Sambles, "Photoluminescence from dye molecules on silver gratings," *Optics Communications*, vol. 122, issue 4-6, pp. 147-154, Jan. 1, 1996.

R. R. Chance, A. Prock, and R. Silbey, "Molecular Fluorescence and Energy Transfer Near Interfaces" in Advances in Chemical Physics, ed by I. Prigogine and S.A. Rice, eds, vol. 37, 1, Wiley, 1978.

* cited by examiner

STANDOFF OPTICAL DETECTION PLATFORM BASED ON SURFACE PLASMON-COUPLED EMISSION

CROSS-REFERENCE TO RELATED APPLICATIONS

The present patent application claims priority to the provisional patent application identified by U.S. Pat. No. 60/647,157 filed Jan. 26, 2005, the entire content of which is hereby incorporated herein by reference.

SUMMARY OF THE INVENTION

In general, the present invention relates to an innovative free-space standoff optical detection platform for any detection system having a scheme based on spontaneous emissions, such as for example, fluorescence detection systems.

More particularly, the present invention relates to a detection system with a detection platform having "SPCE beads". In one embodiment, the SPCE beads are dielectric spheres coated with a thin metal layer, which supports surface plasmon resonance (SPR) at an operation wavelength of the system. The SPCE beads provide additional levels of enhancement, including excitation level and emission collection efficiency. As such, the SPCE beads can be used for high efficiency standoff detection. Further, the size independency and low-cost material (e.g. glass or polymer) of the SPCE beads allow the beads to be spread over a target region and interrogated over a distance.

For an interrogation scheme utilizing electromagnetic excitation, the SPCE beads amplify the field strength of the excitation via the lens effect and SPR enhancement. The spontaneous emitting signal is collected via the coupling between the SPR and emission. Generally, the surface plasmon-coupled emission (SPCE) signal propagates in the beads in a curved path dictated by the SPR condition. Further, the SPCE signal is collimated by the beads and directed back to the standoff interrogator. The result is a high collection efficiency and a high signal-to-noise ratio.

In one embodiment of the present invention, the detection system is for fluorescence detection, and fluorescence reporters are coated on the outer surface of SPCE beads. Upon the presence of an analyte, the emitting signals produced by the fluorescence reporters change. As such, the change in the emitting signals can be utilized to indicate the detection of the analyte by the detection system. Use of the coated SPCE beads for fluorescence detection in accordance with present invention significantly improves both excitation level and signal collection efficiency, thereby overcoming problems experienced by traditional standoff fluorescence detection schemes.

In one embodiment, the present invention is directed to a multilayered spherical structure for harvesting an optical spontaneous emission via surface plasmon coupled effect from a layer of emitting material, and directing the emission in a direction of an incoming excitation in a collimated fashion. The multilayered spherical structure is provided with a low loss dielectric spherical core, a metallic layer, a spacer layer, and a layer of emitting material. The metallic layer (e.g., selected from a group consisting of aluminum, silver, and gold) is capable of supporting surface plasmon resonance at the emission wavelength. The metallic layer is deposited on top of the low loss dielectric spherical core. The spacer layer is constructed of a dielectric material with a thickness from 5 to 100 nm. The spacer layer is positioned on the metallic layer. The layer of emitting material is deposited on top of the spacer layer and has a thickness less than 500 nm. The optical spontaneous emission can be generated from a technology selected from the group consisting of fluorescense, Raman scattering, and second harmonic generation. A diameter of the said multilayer structure may be between one to a hundred wavelength of the optical spontaneous emission.

As discussed above, the multilayered spherical structure can be used for a variety of purposes. For example, the layer of emitting material coated on the spacer layer of the multilayered spherical structure can be excited from a standoff distance with a light source, such as a broadband source, a light emitting diode, a narrowband source, or a laser. The standoff distance is sufficient to cause a plane wave incidence between the excitation light and the emitter. The plane-wave excitation light is focused by the low loss dielectric core onto a backside surface of the structure where the emitter is deposited.

The optical spontaneous emission is preferably collimated and directed in a direction of the incoming excitation. In one embodiment, the optical spontaneous emission is first coupled into a surface plasmon resonance supported by the thin metallic layer and then emitted into a higher refractive index spherical core at a specified polar angle. While the emission is still coupled with the surface plasmon resonance within the near field range from the metallic layer, which is conformed with the low loss dielectric spherical core, the coupled emission propagates along the metallic surface and keeps changing its propagation direction due to the curvature of the metallic layer until the emission may have a desired exit direction. Preferably, there is no confinement in the azimuthal angle so that the emission will be a ring shape inside the low loss dielectric spherical core. The ring shape emission will preferably be further refracted when the emission exits the low loss dielectric spherical structure and propagates back to the origin of the excitation. Due to the symmetry provided by the spherical shape all the shape emission can be directed back to where the excitation comes from.

DETAILED DESCRIPTION OF THE INVENTION

The coupling of surface plasmon resonance (SPR) and nearby spontaneous emission has been observed even before 1980. Since the discovery of surface plasmon-coupled emission (SPCE) in 1975, there has been abundant literatures reporting on both related experimental and theoretical works [W. H. Weber, *Optics Letters*, 1979; R. E. Benner, *Optics Communications*, 1979; I. Gryczynski, *Analytical Biochemistry*, 2004; and G. W. Ford, *Physics Reports*, 1984]. This interesting phenomenon was more recently demonstrated in a 2004 paper authored by Lakowicz [J. R. Lakowicz, "Radiative decay engineering 3. Surface plasmon-coupled directional emission," *Analytical Biochemistry*, 324, 153, 2004.].

It has been shown that the fluorescence of molecules nearby the metal film can be coupled into the surface plasmon (SP) mode, re-radiated out penetrating through metal, and then focused at a well-defined angle [W. H. Weber, *Optics Letters*, 1979; R. E. Benner, *Optics Communications*, 1979]. This angle generally corresponds to the "minimum total reflection angle", which is often used to generate SPR in the Kretschmann configuration (i.e., the SPCE emission angle is the same as the SPR excitation angle). Since there is a one-dimensional confinement applied to the emission, the SPCE radiation pattern is a cone, as shown for example in FIG. 1.

Figure 1:
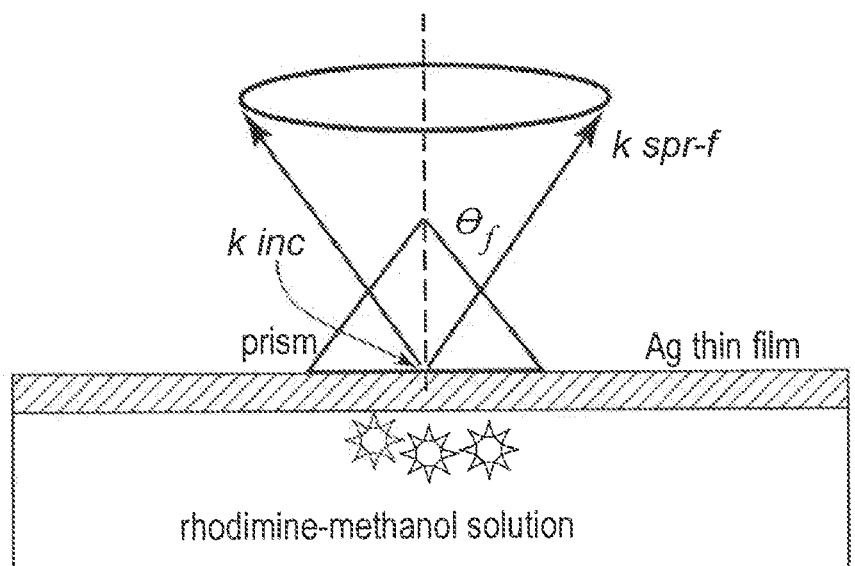
FIG. 1 shows a prior art experiment setup of SPCE excitation.
Figure 2:
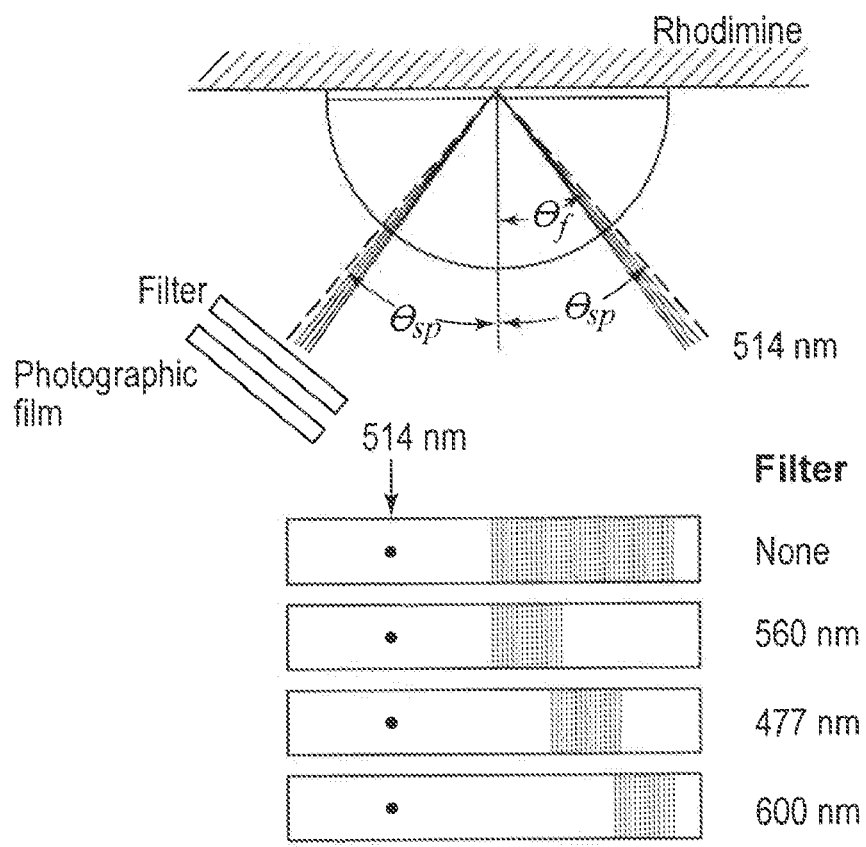
FIG. 2 shows prior art experimental results.

Experiments have been conducted, such as the one by Weber, to demonstrate the effect of surface plasmon-coupled emission (SPCE) [W. H. Weber, *Optics Letters*, 1979]. As shown in FIG. 1, Weber's experiment included a rhodamine-methanol solution which was excited by a p-polarized Ar laser (514.5 nm) through a high refractive index prism and a 75-nm thick Ag film. FIG. 2 demonstrates since the spectral bandwidth of the emission is broad, the range of the corresponding SP angle is also large, and the emission cone has thick width. When this emission cone was projected onto a linear photograph plate, a wide band was shown. If a color film is used for the same experiment, it will have rainbow-like color bands. This is essentially a "SPR grating", which emits light of different colors into different angles.

A thinner cone (or linear band) can be achieved with a narrow-band filter, which limits the spectral content and hence the cone width. The opening angle of the cone becomes smaller as the central wavelength of the filter shifts to longer wavelength, which agrees to the SPR excitation condition well [W. H. Weber, *Optics Letters*, 1979].

Figure 3:
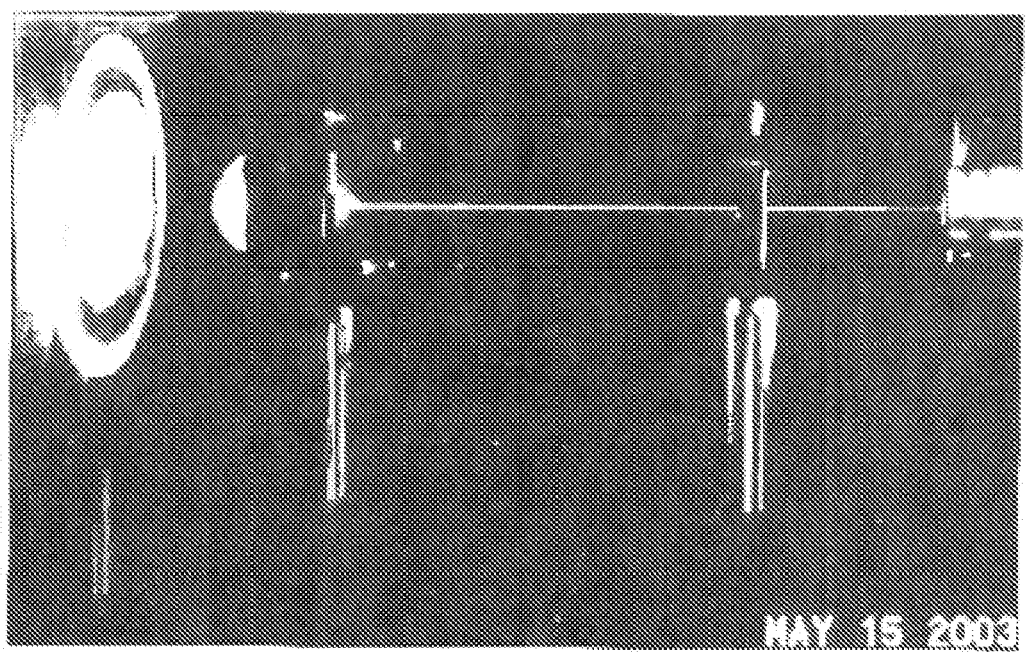
FIG. 3 shows a rainbow-like SPCE emission cone generated by an SPR grating effect.

Lakowicz's group also demonstrated the SPR grating effect in their recent publication [J. R. Lakowicz, *Analytical Biochemistry*, 2004.] by exciting a multiple fluorophores mixture and generating a rainbow cone, as shown in FIG. 3.

There were also several theoretical works published in the early studies which model such phenomenon [W. H. Weber, *Optics Letters*, 1979 and G. W. Ford, *Physics Reports*, 1984.]. The SPR grating effect and the preferential emission of SPCE through metal thin film into the high refractive index (prism) side can be understood by the wavenumber (also known as the propagation constant or momentum) matching criteria:

$$k_0 n_p \sin \theta_f = \text{Re}[k_{sp}], \quad (1)$$

where $k_0$, $k_{sp}$, $n_p$, and $\theta_f$ are the free-space wavenumber, SP wavenumber, refractive index of prism, and SPCE emission angle respectively. As the SP wavenumber, $$k_{sp} = k_0 \sqrt{\frac{\varepsilon_m \varepsilon_s}{\varepsilon_m + \varepsilon_s}}$$

where $\varepsilon_m$, $\varepsilon_s$ are the permittivities of the metal and sample solution, changes at different emission wavelength due to the material dispersion, the emission angle shifts correspondently.

Figure 4:
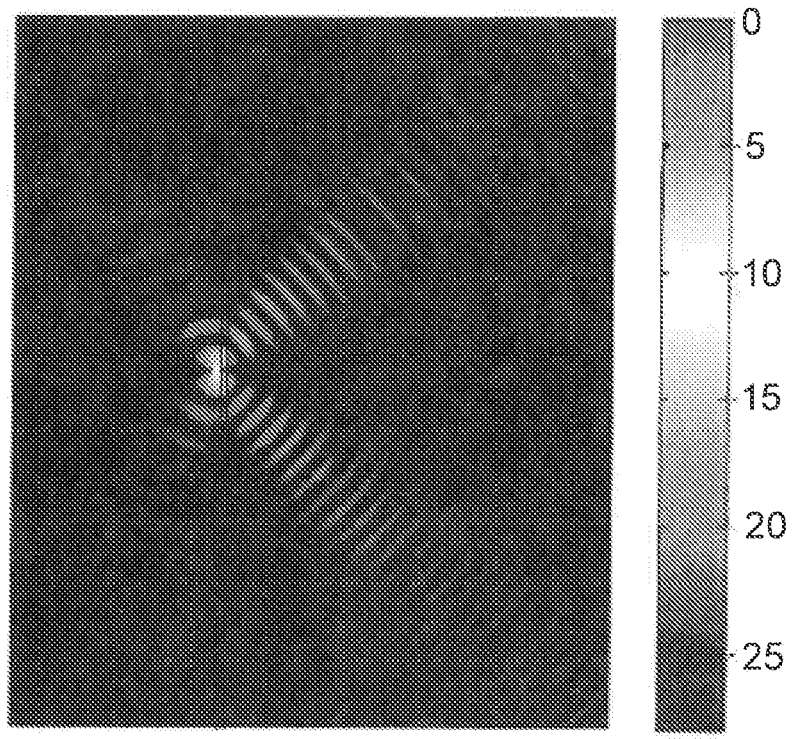
FIG. 4 shows a dipole field coupled into a SPCE, the intensity being displayed in dB scale.

The SPCE can be modeled as a dipole emitter located in the proximity of metal structure. FIG. 4 shows a SPCE emission pattern simulated by using the finite difference time domain (FDTD) method. The black vertical lines indicate the boundary of metal layers. The left side is free space and the right side is filled with high refractive index material (e.g. glass). A dipole normal to the metal surface emits preferentially to the high refractive index side at the SPR excitation angle.

The potential applications of SPCE is significant since any spontaneous emission process, such as fluorescence, flourescence resonance energy transfer (FRET), Raman scattering, second harmonic generation (SHG), etc., may take advantage of the SPCE phenomenon. More particularly, the use of SPCE offers highly desirable features for fluorescence-related sensing applications. Such features include:

1. High Efficient Fluorescence Collection
2. Background Noise Reduction
3. Fluorescence Intensity Enhancement
4. Photostability Improvement Generally, due to the isotropic emission pattern, the common spontaneous emission collection efficiency is about 1% [J. R. Lakowicz, *Analytical Biochemistry*, 2004]. However, the SPCE has an emission pattern that essentially focuses itself into a narrower spatial distribution. This 1D emission confinement not only improves the signal collection efficiency, but also reduces background noise due to reduced data collection volume. However, only the vertically oriented dipole has the high probability of SPR coupling. As such, the averaging effect (among vertical and horizontal orientation) dilutes the maximum harvest efficiency to about 50~60%. However, this still provides significant improvement.

The fluorescence intensity enhancement comes from several factors. First, the excitation may be locally amplified via the surface plasmon resonance SPR) enhancement. Secondly, the radiative lifetime may be reduced due to the change of photonic mode density (PMD) around the emitter, and hence the quantum yield efficiency is increased, as discussed further below. Finally, the non-radiative decay is reduced in the competitive process, which results less damage onto fluorescencing molecules and improves the photostability.

The fluorescence is a radiative decay, which competes with several other non-radiative decay mechanisms. By reducing the radiative decay lifetime (or increasing the radiative decay rate), the quantum yield can be increased and the fluorescent intensity can be enhanced. It is well known that the radiative decay can be engineered by the surrounding PMD. The spontaneous emission usually interacts with the PMD via the evanescent field (near field). Enderlein has conducted some theoretical studies about such effect by modeling it as the dipole-interface interaction using the semi-classical electromagnetic theory [J. Enderlein, *Applied Optics*, 1999. & J. Enderlein, *Chemical Physics*, 1999]. The modification of FRET due to the changing PMD can also be modeled as the resonance dipole-dipole interaction (RDDI) using the similar approach. However, the evanescent field generated near the noble metal surface via SPR is much stronger and extends farther than the one near the dielectric interface via total internal reflection (TIR). Therefore, the modification on the emission due to SPR is a more dramatic than its counter part produced by refractive index contrast [J. R. Lakowicz, *Analytical Biochemistry*, 2004]. This fact grants SPCE, which utilizes SPR, a stronger improvement over other techniques of coupling spontaneous emissions.

The effect of presenting a metal surface to the fluorescencing molecules can be quite different, depending on the newly created photonic mode density (PMD). The presence of metal introduces a new pathway or alters the existing mechanism of the decay processes, which may either boost the radiative rate and hence fluorescence enhancement or promote non-radiative decay and hence fluorescence quenching. Many theoretical works have been conducted to try to understand the behavior.

Figure 5:
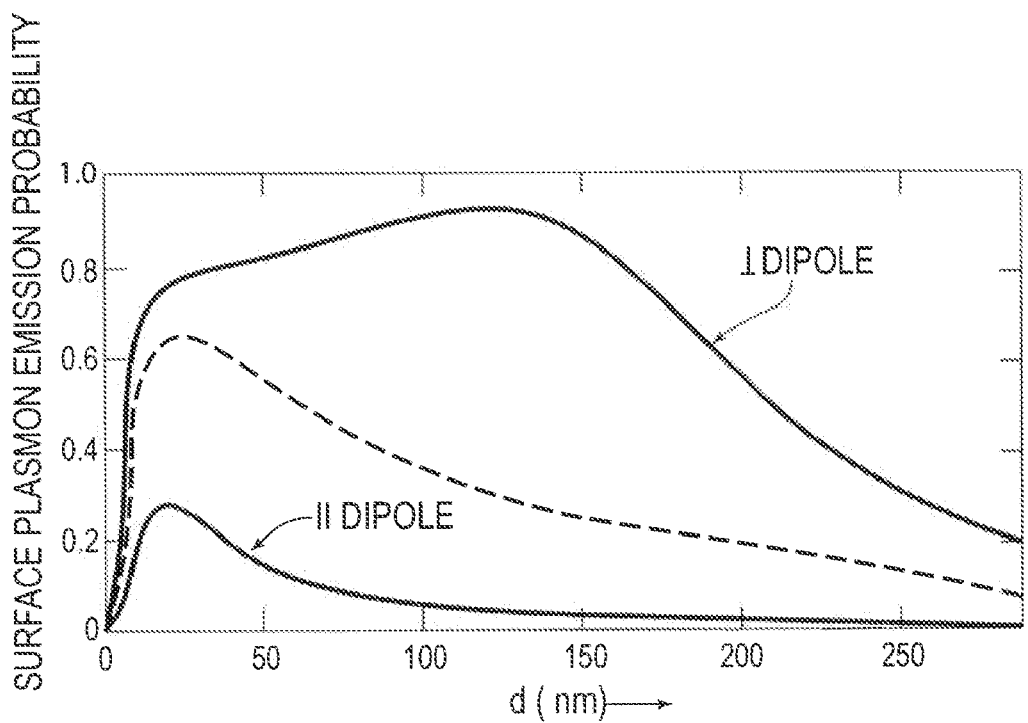
FIG. 5 shows a calculated probability of SP emission of an Ag film.

The probability of the SP-coupled radiative decay rate has been calculated by Weber in 1979 [W. H. Weber *Optics Letters*, 1979.], which is based on Chang's equation [R. R. Chance, *Advances in Chemical Physics*, 1978.]. FIG. 5 shows that the probability SPCE can be as high as 93% when the fluorescing molecule is vertically oriented and 120-nm away from the metal surface. However, the horizontally oriented molecule has much lower SPCE probability under the same condition. In an orientation-randomized scenario, the averaged SPCE is presented as a dashed line in the figure. The parameters for this prediction are noted in the figure caption.

Ford et al. also published similar calculations [G. W. Ford, *Physics Reports*, 1984.] in 1984. It presents the relative decay probability of both non-radiative and radiative mechanisms. It can be seen that the non-radiative decay (dotted lines) dominants when the molecule-metal separation is under 10-nm for both vertically ($\perp$) and horizontally ($\parallel$) oriented molecules. As the separation increases, the SPCE-related decay (solid lines) rises up quickly for the vertically oriented molecule but not for the horizontal one.

The SPCE coupling range can be rather long that it actually peaks at around 120 nm, which agrees well with Weber's results. The free-space non-SPCE related radiative decay also has been presented as dashed lines. At about 120 nm away from metal surface, the free-space radiative decay actually dominants for the horizontally oriented molecules. Therefore, the preferential emission characteristic is "diluted" in the orientation-randomized case. Both works discussed above were cited by Lakowicz [J. R. Lakowicz, *Analytical Biochemistry*, 2004], who estimates the emission harvest efficiency can be still up to 60% under the averaged results.

Ultimately, these previous studies indicate that the presence of metal should be able to enhance the fluorescence as long as the separation of the fluorophores and metal surface is well controlled. Several other experimental works have also successfully demonstrated this capability.

The above-discussed advantages of SPCE are utilized in the present invention for an innovative standoff light emission detection system, which can be used for example in fluorescence detection. While the detection system will be generally described herein with reference to the use of fluorescence by way of illustration, it should be understood that the present invention contemplates the use of any spontaneous emission process.

Figure 6:
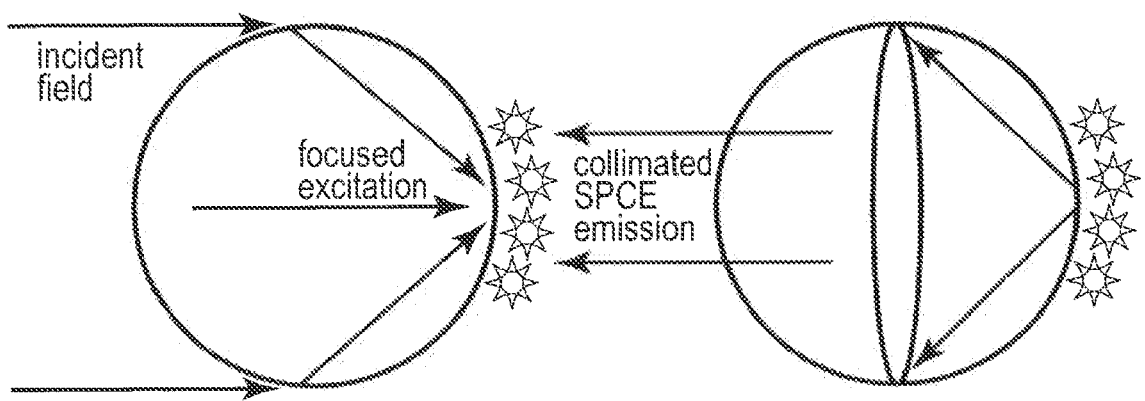
FIG. 6 shows a concept of a SPCE light-emission collimation transmitter constructed in accordance with the present invention.
Figure 8:
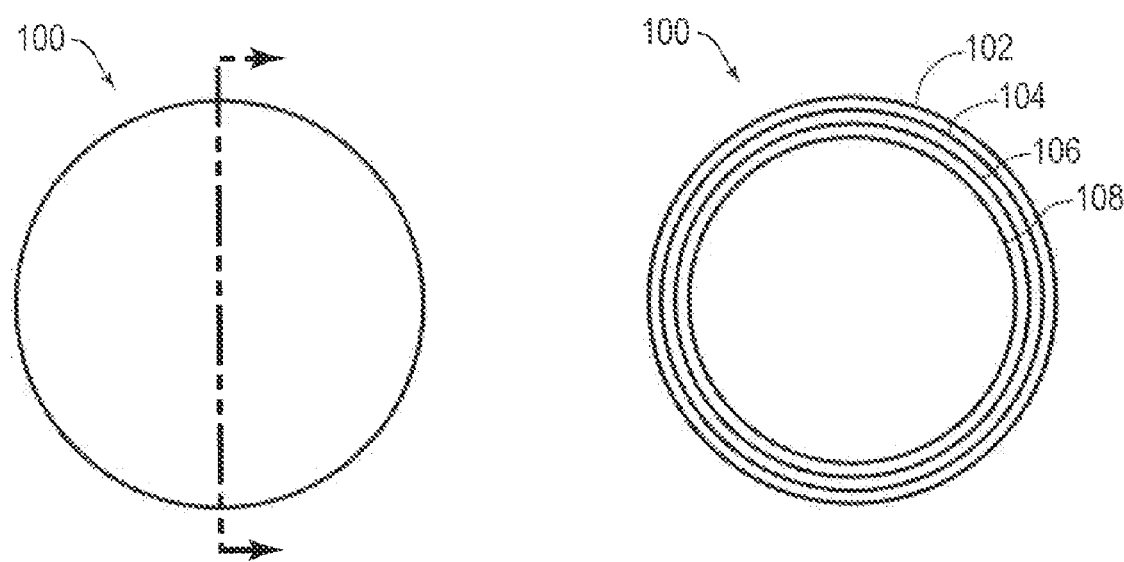
FIG. 8 shows a cross-sectional view of the multilayered spherical structure constructed in accordance with the present invention.

Referring now to the drawings, and in particular to FIGS. 6 and 8, shown therein and designated by reference numeral 100 is a multilayered spherical structure constructed in accordance with the present invention. In one embodiment, the detection system includes a multilayered spherical structure 100, also referred to as an "SPCE bead" 100. The SPCE bead 100 includes a dielectric sphere core 108 and a thin metal coating 106, which is capable of supporting surface plasmon resonance. The dielectric sphere 108 can be made of glass or polymer material for example, and the metal coating 106 can be any surface plasmon-supporting metal, such as silver or gold for the visible wavelength. A dielectric spacer layer 104 is positioned on the metallic layer 106. A light emitting layer 102 of the detection system (and other function layers for analyte specificity) is disposed on top of the dielectric spacer layer 104. For example, the SPCE bead 100 can be coated with a fluorescing reporting materials or any spontaneous emission (e.g. Raman scattering) materials.

The coated SPCE bead 100 provides an innovative platform to achieve an extremely high efficient fluorescence transmitter by using SPCE. This illustrates the general concept associated with the use of the SPCE bead 100 of the present invention.

Essentially, the plane wave of an excitation beam (e.g., from an excitation light pump of the system) which is incident into the dielectric sphere 108 of the SPCE bead 100 is focused by the ball lens effect onto the sphere surface at the far side, where the fluorophores coated on the SPCE bead 100 get excited. This is the first enhancement on the excitation strength due to the lens effect.

Since the excitation is incident from the high dielectric material (sphere) 108, it is possible to excite SPR resonance by adjusting the parameters of the sphere 108, the parameters of the metal thin film 106, and the parameters of the fluorophore 102 coating. This is the second excitation enhancement, which is about 10 fold with a thin metal film 106. The enhancement from a thin metal film 106 has much longer-range than the enhancement created via nanoparticles.

The fluorescence from the light emitting layer 102 is coupled into the SPCE bead 100 and forms an emission cone through the metal thin film 106. This emission cone is transmitted in a direction generally back toward the excitation source. Most importantly, the dielectric sphere 108 serves as a ball lens again and collimates the emission cone for further transmission to a standoff detector of the detection system. This provides significant collection efficiency gain. First, the fluorescence emission cone is substantially collected through the ball lens (sphere) 108. As such, it essentially collects the whole $4\pi$ radian square emission instead of a smaller solid angle collection as seen in traditional standoff detection scenarios. Secondly, the emission is sent back via an approximately collimated beam, which reduces spreading loss as seen in FIG. 6.

The innovative concept of using the coated SPCE bead 100 of the present invention can be demonstrated via numerical modeling, as shown for example in a 2-μm dielectric sphere with refractive index n=1.5 at wavelength of 600 nm is simulated with the FDTD method. The ambient environment is assumed air. The thin metal film is not applied in order to reduce the computation expense. However, the emission pattern should be very similar to the case with a thin metal film. All the intensity is plotted in the dB scale.

Figure 7A:
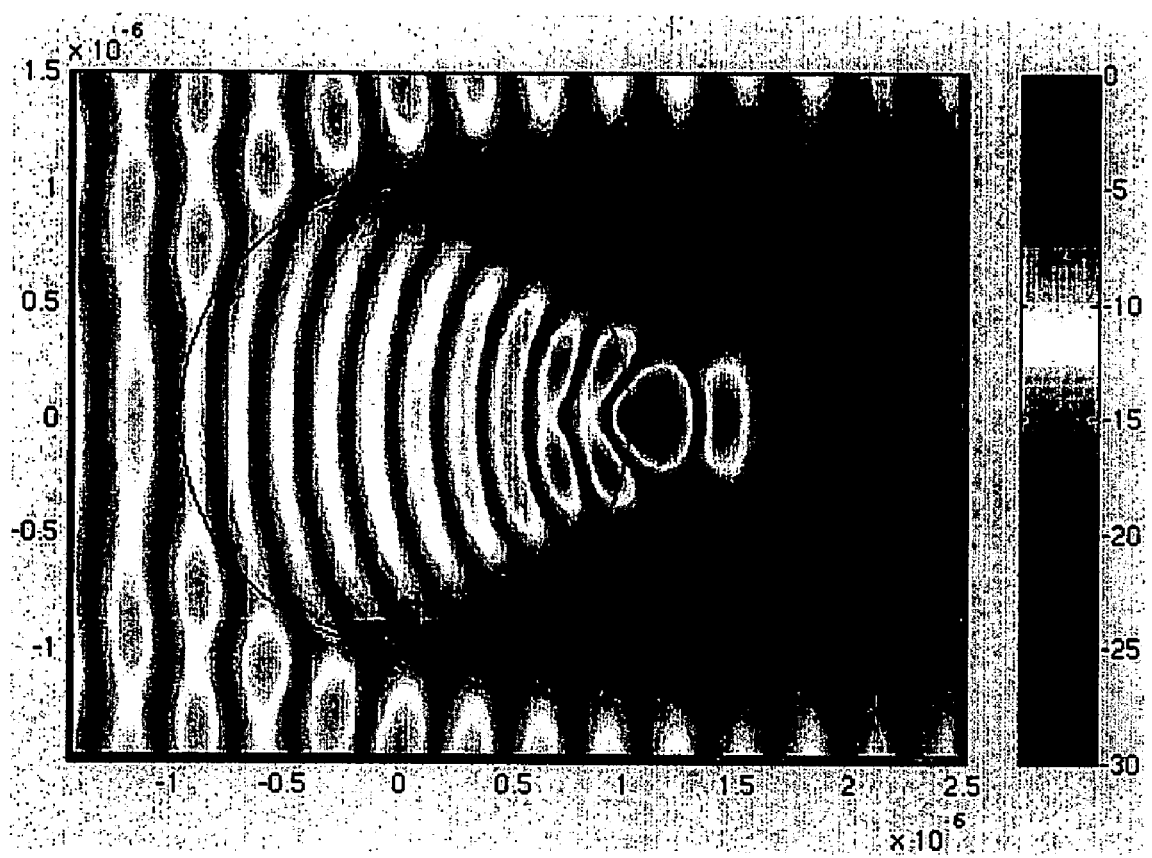
FIG. 7a shows a two-dimensional Finite Difference Time Domain simulation demonstrating an incident field focusing effect.

FIG. 7*a* shows the focusing effect of the incident field coming from the left side, which produces a high-intensity spot on the backside of the sphere, where the focused beam excites the emitters.

Figure 7B:
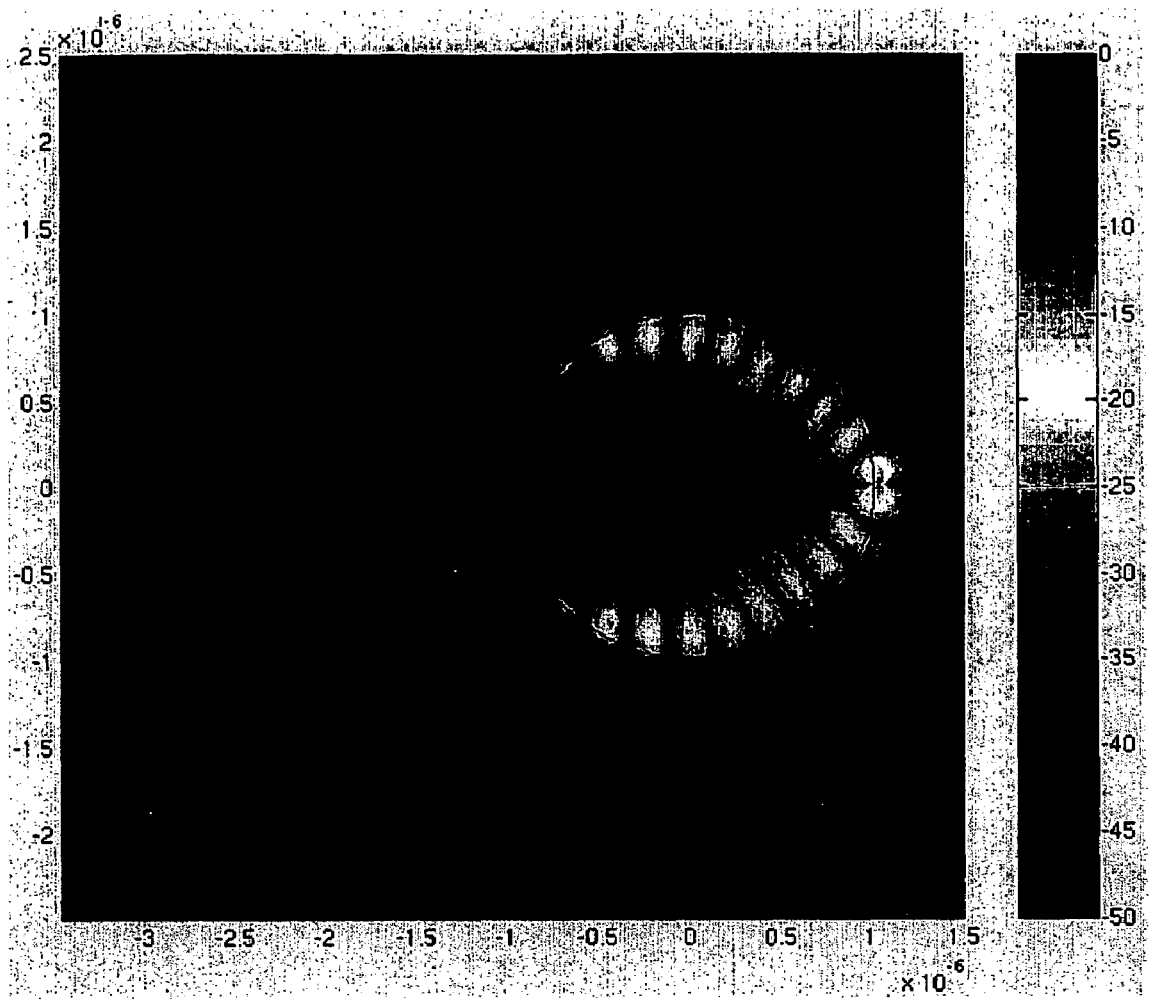
FIG. 7b shows a two-dimensional Finite Difference Time Domain simulation demonstrating an emission collimated back-transmitting effect.

FIG. 7*b* demonstrates that the emission is first coupled into the surface plasmon mode for the SPCE, and then collimated by the sphere. The fluorescence emission is then sent back to the standoff detector with high harvesting efficiency. A single emitter modeled as a vertical dipole normal to the surface is used for the simulation. The simulation results further show another interesting finding that the horizontal dipole on the surface also has a preferential emission pattern in the backward scattering direction.

EXAMPLES

To demonstrate various embodiments and uses of the present invention, the following examples are set forth hereinafter. It is to be understood that the examples are for illustrative purposes only and are not to be construed as limiting the scope of the invention as described herein. The invention is capable of other embodiments, or of being practiced or carried out in various ways.

Example 1

As an example of one application of the present invention, the SPCE bead 100 can be incorporated with a vapor sensing instrument as taught in U.S. Pat. No. 6,558,626, issued to Aker et. al, the entire content of which is hereby expressly incorporated herein by reference. In such an example, a detector for detecting vapors emitted from energetic compounds present in a sample includes a housing, a pump, and a sensing assembly.

The housing defines an enclosed sensing volume. The housing has an inlet and an outlet communicating with the enclosed sensing volume such that a carrier, such as a gas or fluid, can be moved sequentially through the inlet, the enclosed sensing volume and the outlet. The pump communicates with the housing to move the carrier sequentially through the enclosed sensing volume at a predetermined flow rate. The sensing assembly senses the vapors of the energetic compound delivered by the carrier as the carrier passes through the housing. The sensing assembly includes a sensing unit, a source of excitation, at least one light detector, and a converter assembly.

The sensing unit includes a SPCE bead 100 disposed in the housing. The SPCE bead includes a dielectric sphere 108 and a metal layer 106 disposed on the surface of the sphere. A dielectric layer 104 is disposed on top of the metallic layer 106. The sensing unit also includes a light signal emitter layer 102 comprising an amplifying fluorescent polymer, which is disposed on top of the dielectric layer 104 of the SPCE bead 100. The light signal emitter layer 102 is also positioned on the SPCE bead 100 so as to be openly communicating with the enclosed sensing volume of the housing. The intensity of light emitted by the amplifying fluorescent polymer will vary in response to interaction of the amplifying fluorescent polymer with molecules of the energetic compound delivered by the carrier.

The source of excitation of the sensing assembly produces an excitation beam which is positioned so as to be incident into the dielectric sphere 108 of the SPCE bead 100, and thereby focused by the ball lens effect onto a surface of the sphere generally opposite the entry of the excitation beam. Fluorophores of the light signal emitter layer 102, which are nearby the surface where the excitation beam is focused, get excited. The fluorescence from the light signal emitter layer 102 is coupled into the SPCE and forms an emission cone through the metal layer 106 of the SPCE bead 100. This emission cone is transmitted in a direction generally back toward the source of excitation. Further, the dielectric sphere 108 serves as a ball lens again and collimates the emission cone for further transmission to the light detector of the sensing assembly.

The light detector outputs a signal indicative of the intensity of the received portion of the light generated by the amplifying fluorescent polymer. The converter assembly of the sensing assembly receives the signal from the light detector and converts such signal into a format perceivable by an individual.

Example 2

Multiple SPCE beads 100 can be spread over a target region and interrogated over a distance. For example, the beads 100 can be fabricated in a small size (several micron in diameter) and of a light-weight material so that they remain airborne for an extended time. These beads 100 can be projected toward any suspicious "cloud", which may be formed by the airborne aerosols of chemical/bio-chemical warfare agents. The functionalized coating materials of SPCE beads 100 may interact with the aerosols and their emission characteristics change upon specific binding. Such binding event can be remotely interrogated effectively via the excitation amplification and emission concentration scheme provided by the SPCE beads 100 platform. Hence, the standoff detection of aerosol clouds can be achieved The entire contents of each of the following references are hereby expressly incorporated herein.

REFERENCES

1. J. R. Lakowicz, "Radiative decay engineering 3. Surface plasmon-coupled directional emission," Analytical Biochemistry, 324, 153, 2004.
2. W. H. Weber and C. F. Eagen, "Energy transfer from an excited dye molecule to the surface plasmons of an adjacent metal," Optics Letters, 4, 236, 1979.
3. R. E. Benner, R. Dornhaus, and R. K. Chang, "Angular emission profiles of dye molecules excited by surface plasmon waves at a metal surface," Optics Communications, 30, 145, 1979.
4. I. Gryczynski, J. Malicka, Z. Gryczynski, and J. R. Lakowicz, "Radiative decay engineering 4. Experimental studies of surface plasmon-coupled directional emission," Analytical Biochemistry, 324, 170, 2004.
5. G. W. Ford and W. H. Weber, "Electromagnetic interactions of molecules with metal surfaces," Physics Reports, 113, 195, 1984.
6. J. Enderlein, T. Ruckstuhl, and S. Seeger, "Highly efficient optical detection of surface-generated fluorescence," Applied Optics, 38, 724, 1999.
7. J. Enderlein, "Single-molecule fluorescence near a metal layer," Chemical Physics, 247, 1, 1999.
8. R. R. Chance, A. Prock, and R. Silbey, in Advances in Chemical Physics, by 1. Prigogine and S. A. Rice, eds., vol. 31, 1, Wiley, 1978.
9. R. W. Gruhike and D. G. Hall, "Transmission of molecular fluorescenc through a thin metal film by surface plasmon," Applied Physics Letters, 53, 1041, 1988.
10. S. C. Kitson, W. L. Barnes, and J. R. Sambles, "Photoluminescence from dye molecules on silver gratings," Optics Communications, 12, 147, 1996.

Although the foregoing invention has been described in some detail by way of illustration and example for purposes of clarity of understanding, it will be apparent to those skilled in the art that certain changes and modifications may be practiced without departing from the spirit and scope thereof, as described herein. Also, it is to be understood that the phraseology and terminology employed herein is for purpose of description and should not be regarded as limiting.

What is claimed is:

1. A multilayered spherical structure comprising:
a low loss spherical dielectric core constructed of a material capable of passing an excitation light and an emission light having an emission wavelength;
a metallic layer positioned on the core, the metallic layer supporting surface plasmon resonance, the metallic layer generating a surface plasmon resonance signal in response to receiving the emission light;
a dielectric spacer layer positioned on the metallic layer; and an emitting layer positioned on the spacer layer, the emitting layer having a thickness less than one-half of the emission wavelength, the emitting layer defining a sphere having a diameter between one and one hundred of the emission wavelength and having a curved surface, a first aspect facing the excitation light and a second aspect, and the emitting layer constructed of a material capable of generating the emission light in response to receiving the excitation light, wherein the excitation light enters the sphere at the first aspect and propagates to the second aspect of the emitting layer through the dielectric core, the metallic layer, and the dielectric layer; and wherein the emitting layer generates the emission light at the emission wavelength in response to receiving the excitation light, a portion of the metallic layer positioned adjacent to the second aspect receiving the emission light from the emitting layer through the spacer layer and generating the surface plasmon resonance signal at the emission wavelength in response, the curved surface of the sphere coupling the surface plasmon resonance signal into the dielectric core to collimate the emission light whereby the collimated emission light exits the sphere at the first aspect.

2. The multilayer spherical structure of claim 1, wherein an analyte specific reagent layer is positioned on the emitting layer such that the emission light generated therein defines the structure being exposed to said analyte specific chemical, biological, radiation, or explosive substance.

3. The multilayer structure of claim 1, wherein the metallic layer is selected from a group consisting of aluminum, silver, platinum, and gold.

4. The multilayer structure of claim 1, wherein the emitting layer is excited from a standoff distance of at least one thousand emission wavelength.

5. The multilayer structure of claim 4, wherein the excitation light standoff distance is sufficient to define a plane wave incidence between the excitation light and the structure.

6. The multilayer structure of claim 1, wherein the excitation light is generated by a broadband source.

7. The multilayer structure of claim 6, wherein the excitation light is generated by a light emitting diode.

8. The multilayer structure of claim 1, wherein the excitation light is generated by a narrowband source.

9. The multilayer structure of claim 8, wherein the excitation light is generated by a laser.

10. The multilayer structure of claim 1, wherein the collimated emission light exiting the first aspect is directed substantially in, but reverse to the direction of the excitation light.

* * * * *